United States Patent [19]
Desantis et al.

[11] Patent Number: 6,096,317
[45] Date of Patent: Aug. 1, 2000

[54] ST. JOHN'S WORT AND METHYL DONOR COMPOSITION AND USES THEREOF

[75] Inventors: Debbie A. Desantis, Coral Springs; Nader Fotouhi, Boca Raton, both of Fla.

[73] Assignee: Rexall Sundown, Boca Raton, Fla.

[21] Appl. No.: 09/229,445

[22] Filed: Jan. 13, 1999

Related U.S. Application Data

[60] Provisional application No. 60/071,287, Jan. 13, 1998.

[51] Int. Cl.[7] .................................................. A61K 35/78
[52] U.S. Cl. .................... 424/195.1; 514/561; 514/276
[58] Field of Search ............................. 424/195.1, 279.1, 424/439; 514/561, 276

[56] References Cited

U.S. PATENT DOCUMENTS

| | | | |
|---|---|---|---|
| 4,435,424 | 3/1984 | Wurtman | 424/319 |
| 4,795,638 | 1/1989 | Ayache et al. | 424/195.1 |
| 4,973,467 | 11/1990 | Sahley | 424/439 |
| 5,047,435 | 9/1991 | Lavie et al. | 514/732 |
| 5,273,754 | 12/1993 | Mann | 424/440 |
| 5,453,428 | 9/1995 | Kaminski | 514/279 |
| 5,470,846 | 11/1995 | Sandyk | 514/159 |
| 5,514,714 | 5/1996 | Meruelo et al. | 514/561 |
| 5,545,670 | 8/1996 | Bissbort et al. | 514/561 |
| 5,798,101 | 8/1998 | Haveson | 424/195.1 |
| 5,820,867 | 10/1998 | Bewicke | 424/195.1 |
| 5,834,443 | 11/1998 | Masiello | 514/44 |

FOREIGN PATENT DOCUMENTS

| | | | |
|---|---|---|---|
| 79428 | 2/1983 | Romania | A61K 9/08 |

*Primary Examiner*—Jean C. Witz
*Attorney, Agent, or Firm*—Burns, Doane, Swecker & Mathis, L.L.P.

[57] ABSTRACT

A therapeutic composition and method are provided for mood enhancement, regulation and the treatment of depression and anxiety, and the relief of PMS associated symptoms in mammals. The composition comprises St. John's Wort (*Hypericum perforatum*) and a methyl donor, such as S-adenosylmethionine.

15 Claims, No Drawings

ST. JOHN'S WORT AND METHYL DONOR COMPOSITION AND USES THEREOF

This application claims the benefit of priority under 35 U.S.C. §119 of provisional application Ser. No. 60/071,287, filed Jan. 13, 1998, the content of which are hereby incorporated by reference.

BACKGROUND OF THE INVENTION

1. Field of the Invention

The present invention relates to therapeutic compositions for mood enhancement and regulation and the treatment of depression and anxiety, and the relief of premenstrual syndrome ("PMS") associated symptoms in mammals.

2. Description of the Related Art

St. John's Wort (*Hypericum perforatum*) is an herb containing hypericin, flavanoids, phenols, tannins, and volatile oils. Methanolic extract of St. John's Wort is clinically effective for mood enhancement and in the treatment of depression, and the whole herb, extract, and derivatives thereof are widely used for antidepressive effects, nervous unrest and sleep disturbances.

Studies in rat synaptosomes have shown that the possible effect of the extract results from inhibition of serotonin uptake by postsynaptic receptors. Therefore, it is believed that *Hypericum perforatum* and/or its extract and derivatives exert antidepressant and mood regulating effects through activity in the serotonergic system.

S-adenosylmethionine (SAMe) is a naturally occurring molecule found in all living organisms including yeast, vegetable and all animal species. SAMe is synthesized in the body from methionine and adenosine triphosphate (ATP) in a reaction catalyzed by ATP-methionine S-adenosyl transferase. SAMe is distributed throughout virtually all body tissues where it acts as a substrate in many biological reactions involving enzymatic transmethylation (the process by which a methyl group is transferred to different acceptors).

Over the past two decades, a number of studies have demonstrated the importance of methylation processes in the brain. In particular, it has been established that the central nervous system (CNS) requires for normal functioning an adequate supply of SAMe, the methyl donor. Methylation disturbances, folate and monoamine precursor deficiencies, as well as disruptions in adrenergic, dopaminergic, and serotonergic systems have all been implicated in the etiology of depression. Neurotransmitter synthesis involves methyl group transfer of SAMe. People with depression are believed to have decreased levels of SAMe. Studies have also shown that SAMe stimulates the dopaminergic system and has been shown to be efficacious as an antidepressant presumably through its adrenergic and dopaminergic associated activity.

SUMMARY OF THE INVENTION

The present invention provides a therapeutic composition and method for mood enhancement, regulation and the treatment of depression and anxiety, and the relief of PMS associated symptoms in mammals. The composition comprises St. John's Wort (*Hypericum perforatum*) and a methyl donor such as S-adenosylmethionine.

It is a further primary object of the present invention to provide such a therapeutic composition which is a nutraceutical—that is, a composition which includes only components capable of providing beneficial therapeutic effects.

As their modes of action differ, the combination of a methyl donor such as SAMe and *Hypericum perforatum* (and/or any of its active components or extracts) is believed to exert a synergistic effect for mood en +hancement, regulation, the treatment of depression and anxiety and the relief of PMS associated symptoms. The said combination unexpectedly improves the action of each ingredient by surprisingly complementing their mechanism of action where both serotonergic and non-serotonergic neurotransmitter systems are affected simultaneously and synergistically.

The treatment with *Hypericum perforatum* and/or any of its active components or extracts requires 3–4 weeks for observing clinical efficacy as a mood enhancer/antidepressant. The treatment with methyl donor such as SAMe can be effective in mood enhancement/antidepression following 1–2 weeks of administration. It is another unexpected benefit of the said combination to exert efficacy following short term administration, thereby decreasing significantly the period of administration required for therapeutic effect experienced with either *Hypericum perforatum* or methyl donor alone.

This combination provides superior activity in the serotonergic function of *Hypericum perforatum*, with synergistic benefits of a methyl donor, such as SAMe-mediated methylation reactions in neurotransmitter synthesis.

Optional components may also be added to the therapeutic composition of the invention. Such additives include, but are not limited to folic acid, vitamin B6, vitamin B12, vitamin C, and biopterin, as deficiencies of these nutrients are also thought to contribute to depression and anxiety. Optional enhancing herbal additions to the combination can further include, but are not limited to licorice, ginger, rosemary, ginseng (all species), in either whole herb, any of its active components or extracts thereof, as the chemical constituents of these plant materials provide antidepressant benefits in humans.

DESCRIPTION OF THE PREFERRED EMBODIMENTS

Any and all therapeutic combinations comprised of a methyl donor with *Hypericum perforatum* and/or any of its active components or extracts are within the scope of this invention. The said combination optionally includes other therapeutic ingredients, such as folic acid, vitamin B6, vitamin B12, and vitamin C.

In one aspect, the present invention provides a therapeutic composition for mood enhancement and regulation and for the treatment of depression and anxiety, and the relief of PMS associated symptoms in humans comprising: therapeutic synergistic quantities of *Hypericum perforatum* selected from the whole herb, any of its active components or extracts thereof, in combination with a methyl donor.

In this regard, the methyl donor is essential to obtain the beneficial advantages of the present invention and related but non-methyl containing components, such as precursors or nonmethyl-containing derivatives, do not act in accordance with the invention.

The methyl donor is preferably S-adenosylmethionine. However, other methyl donors may also be used, including 5-methyl-tetrahydrofolate, choline, methionine, betaine and methyl-vitamin B12.

The dose of the *Hypericum perforatum* preferably ranges from 25–10,000 mg in whole herb, any of its active components, or extract form.

The dose of the methyl donor preferably ranges from 10 to 5000 mg.

The therapeutic composition of the invention may comprise additional components, including but not limited to folic acid at 50 to 1000 mcg; vitamin B6 at 10 to 2000 mg; vitamin B12 at 10–3000 mcg and biopterin, its precursors, or derivatives at 25–2000 mg; vitamin C at 30–500 mg; and the whole herb, extract or derivative thereof of licorice, ginger, rosemary and ginseng (all species).

In another aspect, the present invention provides a therapeutic composition for mood enhancement and regulation and for the treatment of depression and anxiety, and the relief of PMS associated symptoms in humans comprising: therapeutic synergistic quantities of *Hypericum perforatum* selected from the whole herb, or any of its active components or extracts thereof in combination with a methyl donor, such as S-adenosylmethionine, wherein a dose of the *Hypericum perforatum* in whole herb, or any of its active components or extracts ranges from 25–10,000 mg.

In a preferred aspect, the invention provides a therapeutic composition for mood enhancement and regulation and for the treatment of depression and anxiety, and the relief of PMS associated symptoms in humans comprising: therapeutic synergistic quantities of *Hypericum perforatum* for activity in the serotonergic system in combination with a methyl donor for methylation processes in neurotransmitter synthesis reactions in humans in need thereof for mood enhancement and regulation and treatment of depression and anxiety, and the relief of PMS associated symptoms.

The present invention also provides a method for effecting mood enhancement and regulation and for treating depression and anxiety, and the relief of PMS associated symptoms in humans comprising the step of administering a therapeutically effective quantity of a therapeutic synergistic composition including *Hypericum perforatum* selected from the whole herb, or any of its active components or extracts thereof, in combination with a methyl donor. Preferably the methyl donor is S-adenosylmethionine.

According to the present invention, the therapeutic composition may be administered by any effective route, but preferably administration is orally or parenterally.

In one aspect, the method of the invention uses a therapeutic composition which further includes a mixture comprising one or more of the following nutrients: folic acid at 50 to 1000 mcg; vitamin B6 at 10 to 2000 mg; vitamin B12 at 10–3000 mcg and biopterin, its precursors or derivatives, at 25–2000 mg; vitamin C at 30–500 mg; and the whole herb, extract or derivative thereof of licorice, ginger, rosemary and ginseng (all species).

Although preferred embodiments of the invention have been described above, it will be appreciated that many modifications and variations of the present invention are possible in light of the above teachings and within the purview of the appended claims without departing from the spirit and intended scope of the invention.

We claim:

1. A therapeutic composition for mood enhancement and regulation and for the treatment of depression and anxiety, and the relief of PMS associated symptoms in humans, said composition comprising *Hypericum perforatum* in combination with a methyl donor in therapeutically effective amounts, said methyl donor selected from the group consisting of S-adenosyl-methionine, 5-methyl-tetrahydrofolate, choline, betaine and methyl-vitamin B12.

2. The composition according to claim 1, wherein the *Hypericum perforatum* is in the form of whole herb, or any of its active components or extracts thereof.

3. The composition according to claim 1, wherein the methyl donor comprises S-adenosylmethionine.

4. The composition according to claim 1, wherein the amount of *Hypericum perforatum* ranges from about 25 to about 10,000 mg in whole herb, or any of its active components or extract forms.

5. The composition according to claim 1, wherein the amount of methyl donor ranges from about 10 to about 5000 mg.

6. The composition according to claim 1, which further comprises at least one component selected from the group consisting of folic acid, vitamin B6, vitamin B12, biopterin, vitamin C, and the whole herb, extract or derivative thereof of licorice, ginger, rosemary or ginseng.

7. The composition according to claim 6, which comprises at least one component selected from the group consisting of folic acid at 50 to 1000 mcg, vitamin B6 at 10 to 2000 mg; vitamin B12 at 10–3000 mcg, biopterin at 25–2000 mg; and vitamin C at 30–500 mg.

8. A therapeutic composition for mood enhancement and regulation and for the treatment of depression and anxiety, and the relief of PMS associated symptoms in humans comprising: therapeutic synergistic quantities of *Hypericum perforatum* for activity in the serotonergic system in combination with a methyl donor for methylation processes in neurotransmitter synthesis reactions in humans in need thereof for mood enhancement and regulation and treatment of depression and anxiety, and the relief of PMS associated symptoms, said methyl donor selected from the group consisting of S-adenosyl-methionine, 5-methyl-tetrahydrofolate, choline, betaine and methyl-vitamin B12.

9. A method for effecting mood enhancement and regulation and for treating depression and anxiety, and the relief of PMS associated symptoms in humans comprising the step of administering to a subject in need of treatment a therapeutically effective amount of a composition comprising *Hypericum perforatum* in combination with a methyl donor.

10. The method according to claim 9, wherein the *Hypericum perforatum* is in the form of whole herb, or any of its active components or extracts thereof.

11. The method according to claim 9, wherein the methyl donor comprises S-adenosylmethionine.

12. The method according to claim 9, wherein the composition is administered orally.

13. The method according to claim 9, wherein the composition is administered parenterally.

14. The method according to claim 9, wherein the composition further comprises a mixture comprising at least one component selected from the group consisting of folic acid, vitamin B6, vitamin B12, biopterin, vitamin C, and the whole herb, extract or derivative thereof of licorice, ginger, rosemary or ginseng.

15. The method according to claim 14, wherein the composition comprises at least one component selected from the group consisting of folic acid at 50 to 1000 mcg, vitamin B6 at 10 to 2000 mg; vitamin B12 at 10–3000 mcg, biopterin at 25–2000 mg; and vitamin C at 30–500 mg.

* * * * *

UNITED STATES PATENT AND TRADEMARK OFFICE
CERTIFICATE OF CORRECTION

PATENT NO. : 6,096,317
DATED : August 1, 2000
INVENTOR(S) : Debbie A. DESANTIS et al.

It is certified that error appears in the above-indentified patent and that said Letters Patent is hereby corrected as shown below:

Column 2, line 4, please delete "en +hancement" and insert therefor --enhancement--.

Column 2, line 57, please delete "nonmethyl-containing" and insert therefor --non-methyl containing--.

Column 2, line 61, delete "5-methyl-tetrahydrofolate" and insert therefor --5-methyltetrahydrofolate--.

Column 4, line 46, delete "S-adenosylmethionine" and insert therefor --S-adenosyl-methionine--.

Signed and Sealed this

Seventeenth Day of April, 2001

Attest:

NICHOLAS P. GODICI

*Attesting Officer*   *Acting Director of the United States Patent and Trademark Office*